United States Patent [19]

Szoeke

[11] Patent Number: 5,478,796
[45] Date of Patent: Dec. 26, 1995

[54] PLANT GROWTH REGULATORY MIXTURE COMPRISING MEPIQUAT AND CYCLANILIDE OR OTHER CYCLOPROPYLMALONIC ACID ANILIDES

[75] Inventor: Tibor Szoeke, Chamelet, France

[73] Assignee: Rhone-Poulenc Agrochimie, Lyons, France

[21] Appl. No.: 205,497

[22] Filed: Mar. 4, 1994

[51] Int. Cl.$^6$ .......................... A01N 43/40; A01N 37/30; A01N 53/12
[52] U.S. Cl. .......................................................... 504/130
[58] Field of Search ................................................ 504/130

[56] References Cited

U.S. PATENT DOCUMENTS

| | | | |
|---|---|---|---|
| 4,153,445 | 5/1979 | Kappel | 71/94 |
| 5,123,951 | 6/1992 | See et al. | 71/86 |

OTHER PUBLICATIONS

*The Agrochemicals Handbook* "Mepiquat–Chloride" 1987.

Primary Examiner—S. Mark Clardy
Attorney, Agent, or Firm—Morgan & Finnegan

[57] ABSTRACT

Compositions having a growth regulatory effect, characterized in that they comprise a mixture of a product A, which is mepiquat chloride, and of a derivative of cyclopropylmalonanilic acid (compound B) of formula (I):

$$(R^1)_p C_6 H_{5-p} - NR^2 - CO - C(C_2H_4) - CO - R^3 - R^4$$

in which:
$R^1$ represents a halogen atom or an alkyl, alkoxy, alkylthio, alkylsulfinyl, alkylsulfonyl, nitro, cyano or acetyl group, it being possible for these various radicals optionally to be substituted by one or a number of halogen atoms;

p is an integer equal to 0, 1, 2 or 3; when there are a number of $R^1$ radicals, the latter can be identical to or different from one another;

$R^2$ is a hydrogen atom or a lower alkyl group; the qualifier lower denotes a group containing 1 to 4 carbon atoms;

$R^3$ is an oxygen or sulfur atom;

$R^4$ is a hydrogen atom, or a cation consisting of an ammonium, alkylammonium, polyalkylammonium, hydroxyalkylammonium or poly(hydroxyalkyl) ammonium group or of an alkali metal or alkaline-earth metal, or an alkyl radical which is optionally substituted, especially by hydroxyl or alkoxy groups.

21 Claims, No Drawings

PLANT GROWTH REGULATORY MIXTURE COMPRISING MEPIQUAT AND CYCLANILIDE OR OTHER CYCLOPROPYLMALONIC ACID ANILIDES

I. TECHNICAL FIELD OF THE INVENTION

1. Subject of the invention

The subject of the present invention is compositions having a growth regulatory effect and more particularly compositions which are useful for the treatment of cereals with a view to increasing resistance to lodging or for the treatment of cotton with a view to shortening vegetation and improving yields.

The invention also relates to a process for the treatment of cereals or cotton having this same aim.

2. State of the prior art

It is always desirable to improve agricultural produce, especially cereals or cotton, both on the quantitative level, as regards the yield, and on the qualitative level. Now, cereals can be affected by nutritional disorders, parasitic attacks or damage of climatic nature caused by storms or the wind, which are mainly revealed by a prone appearance of the crop known as lodging. Thus, lodging, especially if it takes place early, can seriously compromise the yield: even later, it leads to poor ripening of the grain, harvesting difficulties and losses, risks of outgrowth, and the like. It is therefore entirely desirable to increase the resistance to lodging of cereals. This resistance to lodging is related to the stalk height of cereals. A cereal has a greater chance of being rendered prone under the possible action of the adverse phenomena mentioned previously, reinforced by the weight of the grain at the end of the stalk, as the stalk of this cereal becomes higher. It is therefore also entirely desirable to reduce the stalk length of cereals. In the case of cotton, it is advantageous to be able to reduce growth in order to increase the earliness of harvesting while contributing a beneficial effect on the quantity and quality of the fiber yield.

Mepiquat chloride (MC), also known as chloride of mepiquat 1,1-dimethylpiperidine chloride, is widely used by farmers for treating cotton. This compound has the effect of shortening vegetation. This compound inhibits the synthesis of gibberellic acid. The method of action therefore does not involve the formation of ethylene in plants. Moreover, it is obvious that other salts of mepiquat, which is a quaternary ammonium, form part of the present invention.

However, it is always desirable to reduce the amount of chemical products distributed in the environment, especially by reducing the application doses of the products.

Malonanilates have indeed been proposed (WO 87/05781) for participating in plant growth regulatory action but only in the context of products inducing the formation of ethylene in plants, which is not the case with MC.

II. AIMS OF THE INVENTION

One aim of the invention is therefore to provide a composition having a growth regulatory effect which is useful for the problems described above.

Another aim of the invention is to improve crop yields and more especially cereal or cotton yields.

Another aim of the invention is to improve resistance to lodging of cereals.

Another aim of the invention is to reduce or to control the growth of cotton.

Another aim of the invention is to reduce the stalk length of cereals.

Another aim of the invention is to reduce the amount of agrochemical products distributed in the environment.

Another aim of the invention is to make possible the application of agrochemical products at reduced doses.

It has now been found that these aims could be achieved in their entirety or in part by virtue of the compositions according to the invention.

III. DETAILED DESCRIPTION OF THE INVENTION

The compositions having a growth regulatory effect according to the invention are characterized in that they comprise a mixture of a product A, which is mepiquat chloride, and of a compound B, which is a derivative of cyclopropylmalonanilic acid corresponding to the formula (I):

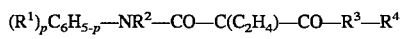

in which:

$R^1$ represents a halogen atom or an alkyl, alkoxy, alkylthio, alkylsulfinyl, alkylsulfonyl, nitro, cyano or acetyl group, it being possible for these various radicals optionally to be substituted by one or a number of halogen atoms;

p is an integer equal to 0, 1, 2 or 3;

when there are a number of $R^1$ radicals, the latter can be identical to or different from one another;

$R^2$ is a hydrogen atom or a lower alkyl group; the qualifier lower denotes a group containing 1 to 4 carbon atoms;

$R^3$ is an oxygen or sulfur atom;

$R^4$ is a hydrogen atom, or a cation consisting of an ammonium, alkylammonium, polyalkylammonium, hydroxyalkylammonium or poly(hydroxyalkyl)ammonium group or of an alkali metal or alkaline-earth metal, or an alkyl radical which is optionally substituted, especially by hydroxyl or alkoxy groups.

According to another aspect of the invention, the compositions according to the invention comprise a mixture of the product A and of the compound B corresponding to the formula (II):

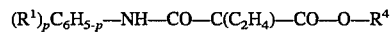

in which:

$R^1$ represents a halogen atom;

p is an integer equal to 0, 1, 2 or 3;

when there are a number of $R^1$ radicals, the latter can be identical to or different from one another;

$R^4$ is a hydrogen atom, or a cation consisting of an ammonium, alkylammonium, polyalkylammonium, hydroxyalkylammonium or poly(hydroxyalkyl)ammonium group or of an alkali metal or alkaline-earth metal, or an alkyl radical.

According to a preferred variant of the invention, the constituents of the compositions according to the invention are:

—for the product A, mepiquat chloride;
—for the compound B, 1-(N-(2,4-dichlorophenyl)carbamoyl)cyclopropanecarboxylic acid, of formula:

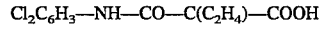

or else its ammonium, alkylammonium, polyalkylammonium, hydroxyalkylammonium or poly(hydroxyalkyl)ammonium salts, or alkali metal or alkaline-earth metal salts, or alternatively its esters.

The product A/compound B ratio by weight, in the compositions according to the invention, is generally between 0.1 and 50, preferably between 1 and 25, when it relates to the treatment of cereals. In the case of cotton, the ratio by weight is generally between 0.1 and 10, preferably between 0.2 and 5 and more preferentially still between 0.5 and 2.

The growth regulatory compositions according to the invention generally contain 0.5 to 95% of the mixture of the compound A and of the compound B.

It can relate to the concentrated composition, that is to say the commercial product combining the two active materials. It can also relate to the dilute composition which is ready to be sprayed on the crop to be treated. In the latter case, dilution with water can be carried out from a commercial concentrated composition containing the two active materials (this mixture is known as "ready mix") or on the mixture which is prepared at the time of use (known as "tank mix") of two commercial concentrated compositions, each containing one active material.

The compositions according to the invention can additionally comprise all the usual additives or adjuvants for plant-protection compositions, especially vehicles, surface-active agents, adherence agents and fluence agents.

In the present description, the term "vehicle" denotes a natural or synthetic, organic or inorganic material with which the active materials are combined to facilitate its application on the plant, on seeds or on the ground. This vehicle is thus generally inert and it must be agriculturally acceptable, especially on the treated plant. The vehicle can be solid (clays, natural or synthetic silicates, silica, resins, waxes, solid fertilizers and the like) or liquid (water, alcohols, ketones, petroleum fractions, aromatic or paraffinic hydrocarbons, chlorinated hydrocarbons, liquefied gases, and the like).

The surface-active agent can be an emulsifying, dispersing or wetting agent of ionic or nonionic type. Mention may be made, for example, of salts of polyacrylic acids, salts of lignosulfonic acids, salts of phenolsulfonic or naphthalenesulfonic acids, polycondensates of ethylene oxide with fatty alcohols or with fatty acids or with fatty amines, substituted phenols (especially alkylphenols or arylphenols), salts of esters of sulfosuccinic acids, taurine derivatives (especially alkyltaurates) or phosphoric esters of polyoxyethylated phenols or alcohols. The presence of at least one surface-active agent is desirable in order to promote dispersion of the active materials in water and their good application on plants.

These compositions can also contain any kind of other ingredients such as, for example, protective colloids, adhesives, thickening agents, thixotropic agents, penetrating agents, stabilizing agents, organic acids, sequestering agents, pigments, dyes or polymers.

More generally, the compositions according to the invention can be combined with all the solid or liquid additives corresponding to the conventional formulating techniques for plant-protection products.

The compositions according to the invention can be in the solid, gel or liquid form and, in the latter case, in the form of solutions or suspensions or emulsions or emulsifiable concentrates. Liquid compositions are preferred, due both to their ease of use and to their simplicity of manufacture.

There may be mentioned, as forms of solid compositions, the powders for dusting or dispersion (with a content of active compounds which can range up to 100%), wettable powders and granules for spreading while dry, as well as dispersable or soluble granules.

Wettable powders (or powders to be sprayed), as well as dispersable granules, generally contain 20 to 95% of active materials and, in addition to the solid vehicle, from 0 to 5% of a wetting agent, from 3 to 10% of a dispersing agent and, when this is necessary, from 0 to 10% of one or more stabilizing agents and/or other additives, such as pigments, dyes, penetrating agents, adhesives, or anticlumping agents, dyes and the like. It is well understood that some of these compositions, such as wettable powders or dispersable granules, are intended to constitute liquid compositions at the time of application.

Mention may be made, as forms of liquid compositions, of solutions, in particular water-soluble concentrates, emulsifiable concentrates, emulsions, suspension concentrates, aerosols or pastes.

The emulsifiable or soluble concentrates most often comprise 10 to 80% of active materials while emulsions or solutions which are ready for application contain, for their part, 0.01 to 20% of active materials. In addition to the solvent, emulsifiable concentrates can contain, when this is necessary, 2 to 20% of suitable additives such as stabilizing agents, surface-active agents, penetrating agents, corrosion inhibitors, dyes or the abovementioned adhesives. From these concentrates, it is possible to obtain, by dilution with water, emulsions of any desired concentration, which are particularly suitable for application to the aerial parts of the plant to be treated. As has already been said, aqueous dispersions and emulsions, for example the compositions obtained by diluting a wettable powder or an emulsifiable concentrate according to the invention with water, are contained within the general scope of the present invention. Emulsions can be of water-in-oil or oil-in-water type and they can have a thick consistency, like that of a "mayonnaise".

The suspension concentrates, also applicable by spraying, are a stable fluid product which does not give rise to thickening or to the formation of a sediment after storage, and they generally contain from 10 to 75% of active materials, from 0.5 to 15% of surface-active agents, from 0.1 to 10% of thixotropic agents and from 0 to 10% of suitable additives, such as pigments, dyes, antifoaming agents, corrosion inhibitors, stabilizing agents, penetrating agents and adhesives and, as vehicle, water or an organic liquid in which the active materials are insoluble or nearly insoluble: certain organic solid materials or inorganic salts can be dissolved in the vehicle to aid in preventing sedimentation or as antigels for water.

The compositions according to the invention are prepared according to processes known per se.

Thus, to obtain powders to be sprayed or wettable powders, the active materials are intimately mixed, in suitable mixers, with the additional substances and the mixture is milled with mills or other grinders. Powders to be sprayed are thereby obtained with advantageous wettability and suspensibility; they can be suspended in water at any desired concentration and these suspensions can be used very advantageously, in particular for application to the aerial parts of plants.

Pastes or suspension concentrates can be produced in place of wettable powders. The conditions and modes of production and use of these pastes are similar to those of wettable powders or powders to be sprayed, part of the milling operation necessary simply being carried out in liquid medium.

Dispersable granules are generally prepared by agglomeration or extrusion or compacting, in suitable granulation systems, of compositions of wettable powder type. Granules for spreading while dry are usually obtained by impregnating a granulated vehicle with a solution or an emulsion of the active materials.

A person skilled in the art will advantageously choose, from these compositions, that or those which are suitable according to the combinations chosen.

The compositions can most often contain the two growth regulators defined above (binary combination) or three (ternary combination) or even four (quaternary combination).

The invention also relates to a process for treating crops intended to protect these crops against lodging and/or to improve yields by controlling growth, characterized in that an effective and non-phytotoxic dose of a composition according to the invention is applied to the leaves.

These compositions are advantageously used so that, in the case of cereals, the mixture consisting of the product A and the compound B is applied at a dose between 100 and 3000 g/ha and preferably between 200 and 2000 g/ha. In the case of cotton, the total application dose is between 10 and 100 g/ha, preferably between 20 and 100 g/ha and more preferentially still between 24 and 48 g/ha. In fact, the product A and the product B are each applied to cotton at a dose between 5 and 50 g/ha, preferably between 10 and 50 g/ha and more preferentially still between 12 and 24 g/ha. Application is advantageously carried out on the aerial parts of the plant, during its growth period. It can be either simultaneous or sequenced.

Cotton and cereals (especially wheat, barley, oats, rye and their hybrids, as well as rape, flax or sunflower) are, among crops to which the compositions according to the invention are applicable, the main crops concerned. However, any other crop is also capable of being treated by the process according to the invention and with the compositions according to the invention.

IV. EXAMPLE

The following example, given without implied limitation, illustrates the invention and shows how it can be implemented.

In this example, the compound B denotes 1-(N-( 2,4-dichlorophenyl)carbamoyl)cyclopropanecarboxylic acid (cyclanilide), of formula:

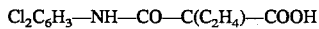

$Cl_2C_6H_3$—NH—CO—$C(C_2H_4)$—COOH

The following treatments are carried out on a cotton patch 2 months after planting:

a) some of the plants are not treated and are thus used as a control, b) plots (3) are treated with 25 g/ha of mepiquat chloride (MC), c) and plots (3) are treated with a mixture contributing 25 g/ha of mepiquat chloride (MC) and 10 g/ha of compound B.

The height of the cotton is measured 24 days after treatment. The mean of the heights is then determined as a function of the treatment. Thus, the control cotton (a) has a mean height of 44.3 inches (112.5 cm). The cotton treated with MC alone (b) has a mean height of 36.1 inches (91.7 cm) and the cotton treated with the mixture (c) has a mean height of 31.9 inches (81.0 cm).

It is therefore clearly seen that the addition of the compound B to MC makes it possible to increase the shortening by about 10 cm with respect to MC alone, i.e. 12% additional shortening for the treatment c) with respect to the treatment b).

I claim:

1. Compositions having a growth regulatory effect, characterized in that they comprise a mixture of a product A, which is mepiquat chloride, and of a derivative of cyclopropylmalonanilic acid (compound B) of Formula (I):

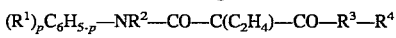

$(R^1)_pC_6H_{5-p}$—$NR^2$—CO—$C(C_2H_4)$—CO—$R^3$—$R^4$ in which:
R$^1$ represents a halogen atom or an alkyl, alkoxy, alkylthio, alkylsulfinyl, alkylsulfonyl, nitro, cyano or acetyl group, wherein said group can be optionally substituted by one or more halogen atoms;

p is an integer equal to 0, 1, 2 or 3; when there are a number of R$^1$ radicals, the latter can be identical to or different from one another;

R$^2$ is a hydrogen atom or a lower alkyl group containing 1 to carbon atoms;

R$^3$ is an oxygen or sulfur atom;

R$^4$ is a hydrogen atom, or a cation consisting of an ammonium, alkylammonium, polyalkylammonium, hydroxalkylammonium or poly(hydroxyalkyl) ammonium group or of an alkali metal or alkaline-earth metal, or an alkyl radical which is optionally substituted by hydroxyl or alkoxy groups.

2. Compositions according to claim 1, characterized in that the compound B corresponds to the formula (II):

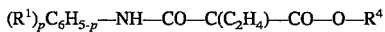

$(R^1)_pC_6H_{5-p}$—NH—CO—$C(C_2H_4)$—CO—O—$R^4$ in which:
R$^1$ represents a halogen atom;

p is an integer equal to 0, 1, 2 or 3;
when there are a number of R$^1$ radicals, the latter can be identical to or different from one another;

R$^4$ is a hydrogen atom, or a cation consisting of an ammonium, alkylammonium, polyalkylammonium, hydroxyalkylammonium or poly(hydroxyalkyl)ammonium group or of an alkali metal or alkaline-earth metal, or an alkyl radical.

3. Compositions according to claim 1, characterized in that:
—product A is mepiquat chloride; and
—compound B is 1-(N-(2,4-dichlorophenyl)carbamoyl)cyclopropanecarboxylic acid, an ammonium, alkylammonium, polyalkylammonium, hydroxyalkylammonium or poly(hydroxyalkyl)ammonium salt thereof, an alkali metal or alkaline-earth metal salt thereof, or an ester thereof.

4. Compositions according to claim 1, characterized in that the product A/compound B ratio by weight is between 0.1 and 50.

5. Compositions according to claim 4, wherein said ratio by weight is between 1 and 25.

6. Compositions according to claim 1, characterized in that the product A/compound B ratio by weight is between 0.1 and 10.

7. Compositions according to claim 6, wherein said ratio by weight is between 0.2 and 5.

8. Compositions according to claim 6, wherein said ratio by weight is between 0.5 and 2.

9. Compositions according to claim 1, wherein said composition contains 0.5 to 95% of a mixture of product A and compound B.

10. Process for the treatment of crops to protect them against lodging and/or to improve yields, characterized in that an effective and non-phytotoxic dose of a composition according to claim 1 is applied to aerial parts of the crops.

11. Process according to claim 10, characterized in that the mixture consisting of the product A and the compound B is applied at a dose between 100 and 3000 g/ha.

12. Process according to claim 11, characterized in that the mixture consisting of the product A and the compound B is applied at a dose between 200 and 2000 g/ha.

13. Process according to one of claims 10 or 11, characterized in that the crop is a cereal.

14. Process according to one of claims 10 or 11, characterized in that the crop is chosen from the group consisting of wheat, barley, oats, rye and their hybrids, rape, flax and sunflower.

15. Process for the treatment of cotton to improve yields and/or to control growth, characterized in that an effective and non-phytotoxic dose of a composition according to claim 1 is applied to aerial parts of cotton.

16. Process according to claim 15, characterized in that the mixture consisting of the product A and the compound B is applied at a dose between 10 and 100 g/ha.

17. Process according to claim 16, characterized in that the mixture consisting of the product A and the compound B is applied at a dose between 20 and 100 g/ha.

18. Process according to claim 16, characterized in that the mixture consisting of the product A and the compound B is applied at a dose between 24 and 48 g/ha.

19. Process according to claim 16, characterized in that the product A and the product B are each applied at a dose between 5 and 50 g/ha.

20. Process according to claim 19, characterized in that the product A and the product B are each applied at a dose between 10 and 50 g/ha.

21. Process according to claim 19, characterized in that the product A and the product B are each applied at a dose between 12 and 24 g/ha.

* * * * *